(12) United States Patent
Wotherspoon

(10) Patent No.: US 8,145,312 B2
(45) Date of Patent: Mar. 27, 2012

(54) POWER SUPPLY CONTROL CIRCUIT, POWER SUPPLY AND BODY IMPLANT

(75) Inventor: Tracy Wotherspoon, Wales (GB)

(73) Assignee: Microsemi Semiconductor Limited, Wiltshire (GB)

( * ) Notice: Subject to any disclaimer, the term of this patent is extended or adjusted under 35 U.S.C. 154(b) by 320 days.

(21) Appl. No.: 12/580,740

(22) Filed: Oct. 16, 2009

(65) Prior Publication Data

US 2010/0100149 A1   Apr. 22, 2010

(30) Foreign Application Priority Data

Oct. 17, 2008   (GB) .................................. 0819032.4

(51) Int. Cl.
*A61N 1/00* (2006.01)
(52) U.S. Cl. .......................................... 607/34; 323/911
(58) Field of Classification Search .................... 607/34, 607/2, 59; 323/201–371, 911
See application file for complete search history.

(56) References Cited

U.S. PATENT DOCUMENTS 3,620,220 A   11/1971   Murphy, Jr.

FOREIGN PATENT DOCUMENTS

| DE | 25 56 840 | 12/1975 |
| EP | 0 162 563 A2 | 11/1985 |
| EP | 0 695 017 A2 | 1/1996 |
| EP | 0 736 828 A2 | 10/1996 |
| GB | 1 354 656 | 5/1974 |

OTHER PUBLICATIONS

Paulpress, Bucket Brigade Could Boost Solar Cell Voltages, Berkeley Lab Center—http://newscenter.lbl.gov Sep. 15, 2011.

*Primary Examiner* — Scott Getzow
(74) *Attorney, Agent, or Firm* — Arent Fox LLP

(57) ABSTRACT

A power supply comprises transistors whose conduction paths are connected in series and whose control terminals receive a reference voltage. The common terminal at one end of the series-connected conduction paths provides a regulator output whereas output terminals of the transistors are connected to charge storage capacitors, which are charged by respective power generators for scavenging energy from the environment. The transistors begin conducting in sequence so that the storage capacitors begin contributing sequentially to the output current as each transistor conducts in sequence. The capacitors are charged up when they are not contributing to the output current.

14 Claims, 4 Drawing Sheets

POWER SUPPLY CONTROL CIRCUIT, POWER SUPPLY AND BODY IMPLANT

CROSS-REFERENCE TO RELATED APPLICATION

This application claims the priority of GB Application No. 0819032.4, filed Oct. 17, 2008, the entire specification, claims and drawings of which are incorporated herewith by reference.

TECHNICAL FIELD

The present invention relates to a control circuit for a power supply. The present invention also relates to a power supply including such a control circuit and to a body implant including such a power supply.

BACKGROUND

There is considerable interest in the using or recycling of ambient energy, which would normally be unused or lost, for example as waste heat, motion or sound. One field of interest relates to large-power generation, for example using wind or solar power. Another field of interest relates to small-scale power generation, for example for powering sensors.

In small-scale industrial or scientific applications, there is a desire to have self-powered sensors which store data and communicate it to a central monitoring station, for example wirelessly or by manual collection. Examples of uses of such sensors include body implants, climate or seismic activity monitoring, animal tracking, process control monitoring, engine management and remote displays. Such sensors are provided at least partly with power by scavenging from their environment, for example using waste energy in the form of heat transfer, solar radiation, material deformation and bio-fuel cells.

In body implants for medical uses such as pacemakers, the physically largest component is generally a battery, which may occupy as much as 50% of the internal volume of such an implant and which thus restricts the space available for electronics. It is desirable to reduce the battery size and/or increase the battery life. Known techniques for achieving this have relied on augmenting the power supply by means of energy derived from mechanical movement, cardiac activity and bio-fuel cells. In safety-critical applications where power must be available continuously, the risk associated with completely removing a battery is unacceptably high. For such applications, self-powered implants generally have to be capable of returning to battery power in the event of failure of a power generator or of insufficient ambient energy to supply the requirements.

For many types of sources of ambient energy, the scavenged energy is generally available in bursts, for example of pulses or alternating current cycles. Such bursts tend to have low repetition rates. For example, in the case of bio-medical scavenging, the repetition rate may typically be between 1 and 10 Hz. When several power generators are used, there is generally no fixed phase relationship between the supply of energy from the individual generators.

FIG. 1 of the accompanying drawings illustrates a typical power supply of known type for providing storage of scavenged energy. A plurality of scavenged energy power generators is connected to inputs $1_1$-$1_N$ of the power supply. In the example shown in FIG. 1, the generators are assumed to be of the alternating current type and are connected via the inputs to corresponding full wave bridge rectifiers $2_1$-$2_N$. The outputs of the bridge rectifiers are connected in parallel across a storage capacitor 3 of sufficiently large capacitance to store sufficient charge for the intended application. One terminal of the capacitor 3 is connected via a diode 4 to a first terminal of a voltage—limiting diode 5, such as a Zener diode, and to the input of a voltage regulator 6, whose output forms the output 7 of the power supply. A back-up battery 8 is provided and has a first terminal connected via another diode 9 to the first terminal of the diode 5 and the input of the regulator 6. Second terminals of the capacitor 3, the diode 5 and the battery 8 are connected to a common line and to the common terminal of the regulator 6.

When the capacitor 3 is charged to a voltage greater than that of the battery 8, the diode 4 is forward-biased and conducts, whereas the diode 9 is reverse-biased and isolates the battery 8. The regulator 6 thus draws power from the charge stored in the storage capacitor 3 (and from any one generator providing sufficient voltage for its bridge rectifier to be conducting). Conversely, when the voltage across the capacitor 3 is below that of the battery 8, the diode 4 isolates the capacitor from the regulator input, which receives power from the battery 8.

The bridge rectifiers $2_1$-$2_N$ are also such that the generator supplying the highest voltage at any time is connected to and charges up the capacitor 3 whereas the bridge rectifiers connected to the other generators are effectively reverse-biased and are unable to conduct. Thus, power generated by the other generators cannot be utilised for charging the capacitor 3 and hence is lost.

FIG. 2 of the accompanying drawings illustrates another known type of power supply comprising an input 1 for connection to a power generator, a full wave bridge rectifier 2, a storage capacitor 3 and a regulator 6 connected to the power supply output 7. The power supply further comprises a switch 10, for example in the form of a metal oxide silicon field effect transistor (MOSFET), for connecting or disconnecting the regulator to or from the capacitor 3 so as to switch the power supply on or off.

In use, the voltage across the capacitor 3 is monitored by means which are not shown in FIG. 2. When the voltage across the capacitor 3 rises to a sufficient value, the switch 10 is closed. Where the power supply forms part of a self-powered wireless sensor, for example, the sensor starts to operate and to transmit data. When the voltage across the capacitor 3 falls to an insufficient value, the switch 10 opens to allow the capacitor to be recharged by the power generator via the bridge rectifier 2. The measuring and transmission of data is therefore unpredictable and generally irregular, which may make such an arrangement unsuitable for many applications.

The power supplies shown in FIGS. 1 and 2 require a relatively large value of storage capacitance, in the form of a single capacitor or a plurality of parallel-connected capacitors, in order to store sufficient charge to supply the power for any significant or useful amount of time. However, this places a substantial stress on the generators, for example, when the capacitor 3 is fully discharged. In this state, the capacitor 3 substantially presents a short-circuit to the generators, which must therefore be capable of working into such a low load. This may also result in a relatively long charge-time. Also, each time the switch 10 of FIG. 10 closes, a high peak current demand may be made and this may apply a relatively large stress to the switch 10, which may raise an issue of reliability.

SUMMARY

According to a first aspect of the invention, there is provided a control circuit for a power supply, comprising N amplifying devices, where N is an integer greater than 1, having main conduction paths connected in series and control terminals connected together to receive a reference voltage, the main conduction path of an Nth of the amplifying devices being connected between an output of the regulator and an Nth circuit node connected to an Nth charge storage device and the main conduction path of each ith amplifying device, for each i such that $1 \leq i < N$, being connected between an (I+1)th circuit node and an ith circuit node, which is connected to an ith charge storage device, at least two of the circuit nodes being connected to respective inputs for connection to respective power generators.

At least some of the charge storage devices may comprise capacitors. All of the charge storage devices may comprise capacitors.

At least one of the charge storage devices may comprise a battery. The first charge storage device may comprise a battery.

Each of the amplifying devices may have a common terminal and an output terminal and the output terminal of each jth amplifying device, for each j such that $1 \leq j \leq N$ may be connected to the jth circuit node.

Each of the amplifying devices may comprise a semiconductor device. The semiconductor devices may be of a same conductivity type. The semiconductor devices may comprise transistors, the control terminals may comprise base or gate terminals, the common terminals may comprise emitter or source terminals, and the output terminals may comprise collector or drain terminals.

At least one of the inputs may be connected to a corresponding one of the charge storage devices and of the circuit nodes via a rectifier.

According to a second aspect of the invention, there is provided a power supply comprising a circuit according to the first aspect of the invention.

The or each input may be connected to a respective power generator. The or each power generator may comprise an energy scavenging generator.

According to a third aspect of the invention, there is provided a body implant including a power supply according to the second aspect of the invention.

It is thus possible to provide an arrangement in which charge may simultaneously be stored from several power generators while power is supplied to a load. Fuller use may therefore be made of energy scavenged from the environment of each power generator. Peak generator loadings and peak current demands may be reduced, which may improve reliability or allow devices of reduced ratings to be used satisfactorily.

Such arrangements may be used in relatively small devices, for example in sensors of the types described hereinbefore. However, such arrangements may also be used in higher power applications, such as wind generators and solar power generators.

BRIEF DESCRIPTION OF THE DRAWINGS

Like reference numerals refer to like parts throughout the drawings.

DETAILED DESCRIPTION

Figure 1:
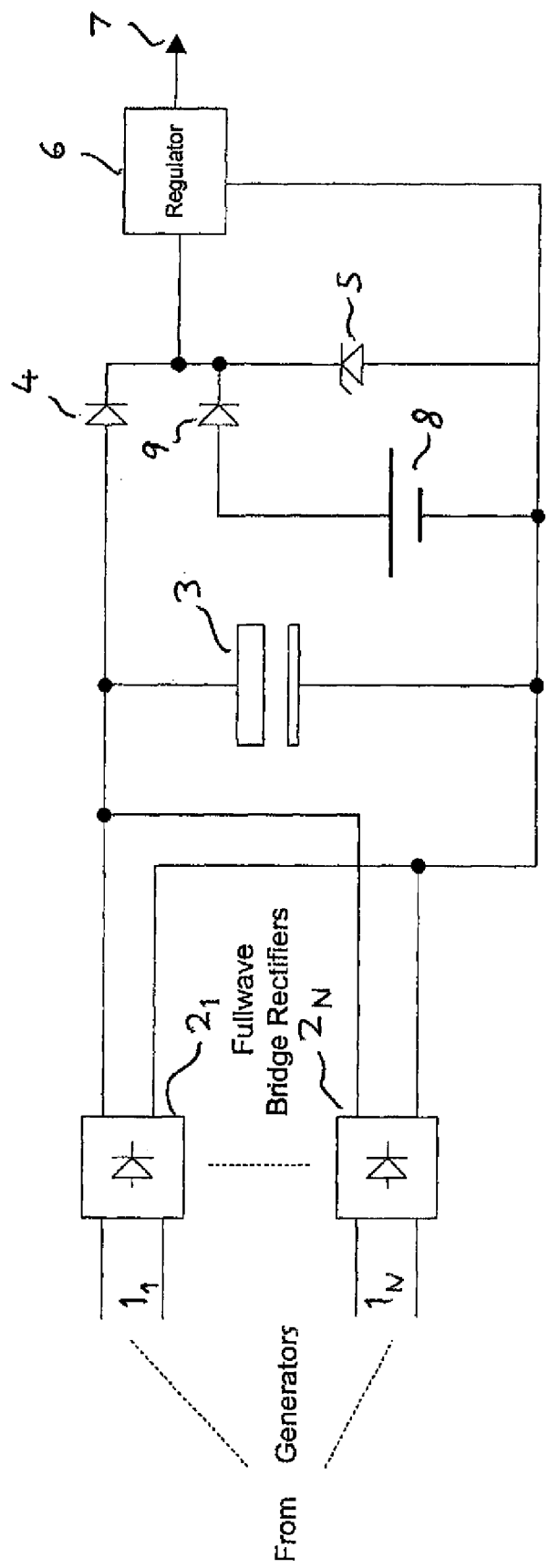
FIG. 1 is a circuit diagram of a known type of power supply.
Figure 2:
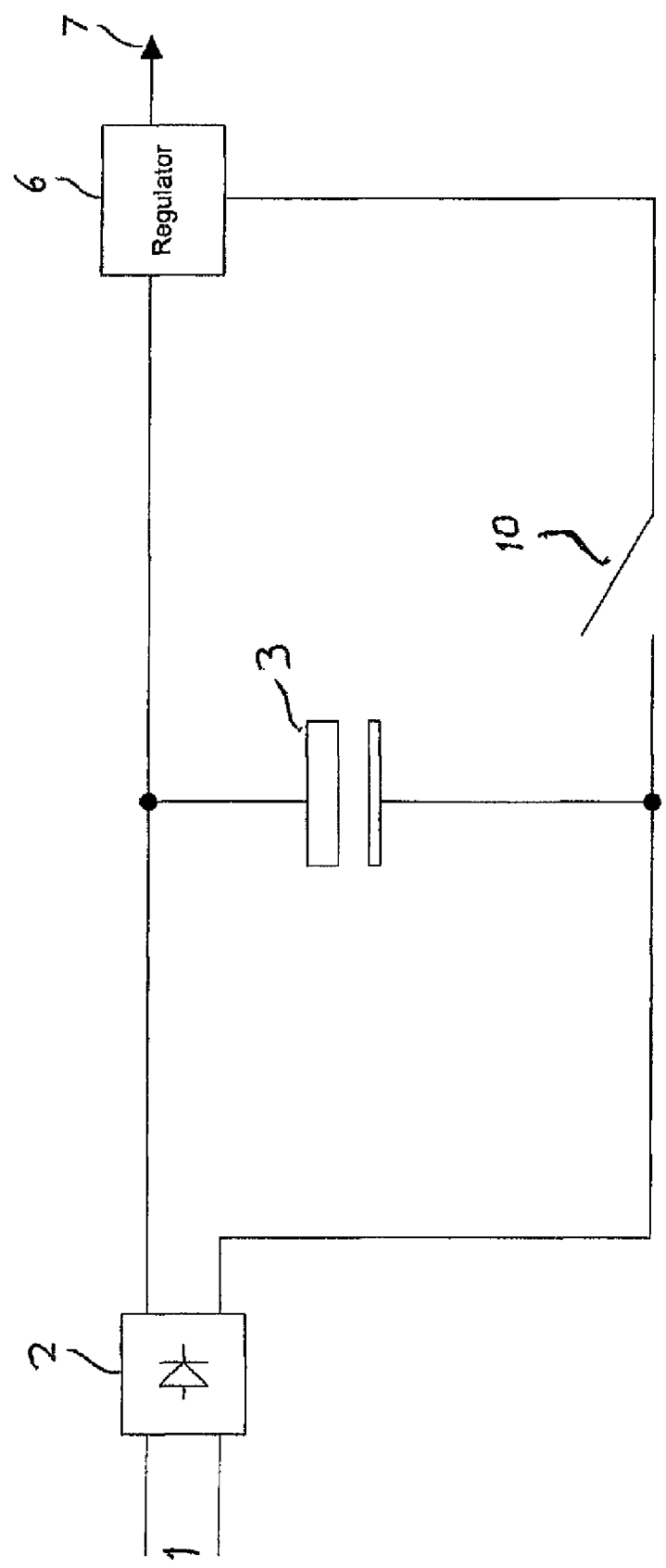
FIG. 2 is a circuit diagram of another known type of power supply.
Figure 3:
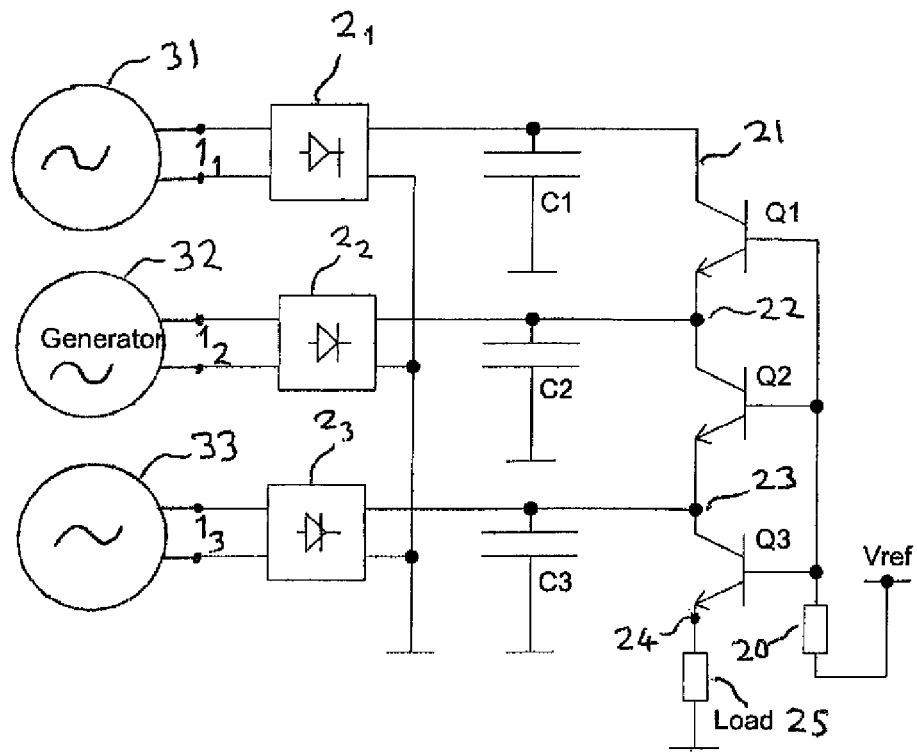
FIG. 3 is a circuit diagram of a control circuit and power supply constituting a first embodiment of the invention.

The control circuit and power supply shown in FIG. 3 has N inputs $1_1$, $1_2$ and $1_3$ (where N may be any integer greater than one but is equal to three in this embodiment) connected to three power generators 31, 32 and 33. The inputs are connected via respective full wave bridge rectifiers $2_1$, $2_2$ and $2_3$ to respective storage capacitors C1, C2 and C3.

Three amplifying devices in the form of semiconductor bipolar transistors Q1, Q2 and Q3 have their control or base terminals connected together and via a resistor 20 to a source of a reference voltage $V_{ref}$. The main conduction paths of the transistors Q1, Q2, and Q3 are connected in series. The main conduction path of the first transistor Q1 is connected between a first circuit node 21 and a second circuit node 22. The main conduction path of the second transistor Q2 is connected between the second circuit node 22 and a third circuit node 23. The main conduction path of the third transistor Q3 is connected between the third circuit node 23 and an output 24 of the regulator, which is shown as being connected to a load 25 illustrated by a resistor.

The transistors Q1, Q2 and Q3 are of the same conductivity type and, in the example shown in FIG. 3, are of NPN type. The output terminals or collectors of the transistors Q1, Q2 and Q3 are connected to the first to third circuit nodes 21, 22 and 23, respectively. Each of the circuit nodes is connected to a respective one of the storage capacitors C1, C2 and C3 and via the respective bridge rectifiers $2_1$, $2_2$ $2_3$ to the respective inputs $1_1$, $1_2$ and $1_3$ for connection to the power generators.

In the embodiment shown in FIG. 3, the generators are all alternating current generators for scavenging energy from their environments. For example, the generators may generate energy from vibration, mechanical motion or an ambient radio frequency field. Alternatively, one or more of the generators may be arranged to supply direct current or single polarity pulsed current, in which case it may be connected directly to the corresponding storage capacitor without the need for a bridge rectifier. Such generators may be of any appropriate type and examples of continuous direct current generators include bio-fuel cells, solar cells, thermal generators and tidal generators. Examples of pulsed generators include piezo impact generators. If necessary to provide the appropriate isolation from the storage capacitors so as to prevent discharge via the generators, single diodes may be provided in place of the bridge rectifiers in the case of direct current generators. The generators are such that they are all capable of generating a voltage which charges the associated storage capacitor. to a voltage greater than $V_{ref}$.

In use, the generators charge the capacitors C1, C2 and C3 via the respective bridge rectifiers $2_1$, $2_2$ and $2_3$ (or directly in the case of direct current generators). When the capacitors are charged to a sufficient voltage, one or more transistors Q1, Q2 and Q3 begins to conduct and to supply power via the output terminal 24 to the load 25. The transistor Q3 regulates the voltage so as to provide a maximum voltage across the load 25 which is lower than the reference voltage $V_{ref}$ by the forward-biased base-emitter voltage of the transistor Q3, which is typically 0.6 volts in the case of a silicon bipolar transistor.

If the voltage across the storage capacitor C3 exceeds ($V_{ref}$–0.6 V), then the transistor Q2 is switched off and the capacitor C3 supplies current to the load 25. However, the generators connected to the inputs and $1_2$ may continue to charge the capacitors C1 and C2 so as to improve the scavenging or recovery of ambient energy. The capacitors C1 and C2 can be charged to a maximum voltage determined by the generators which are charging them, allowing for voltage drops as appropriate through diodes or bridge rectifiers.

During this state, the base-emitter junction of the transistor Q2 is reverse-biased no that the transistor Q2 does not conduct. However, as the capacitor C3 discharges, the voltage at the third circuit node 23 falls, unless the generator connected to the input $1_3$ is capable of supplying the current demands of the load 25. As the voltage at the third circuit node 23 falls, it reaches a value equal to the forward voltage drop of the base-emitter diode of the transistor Q2 below the reference voltage $V_{ref}$, at which point the transistor Q2 begins to conduct. Thus, current is supplied from the capacitor C2 via the transistors Q2 and Q3 to the load 25 to augment current supply from the capacitor C3. Similarly, as the voltage across the capacitor C2 falls, it reaches a value where the transistor Q1 begins to conduct so that the load is supplied by the charge stored in the capacitor C1 together with any residual charge in the capacitors C2 and C3.

Figure 4:
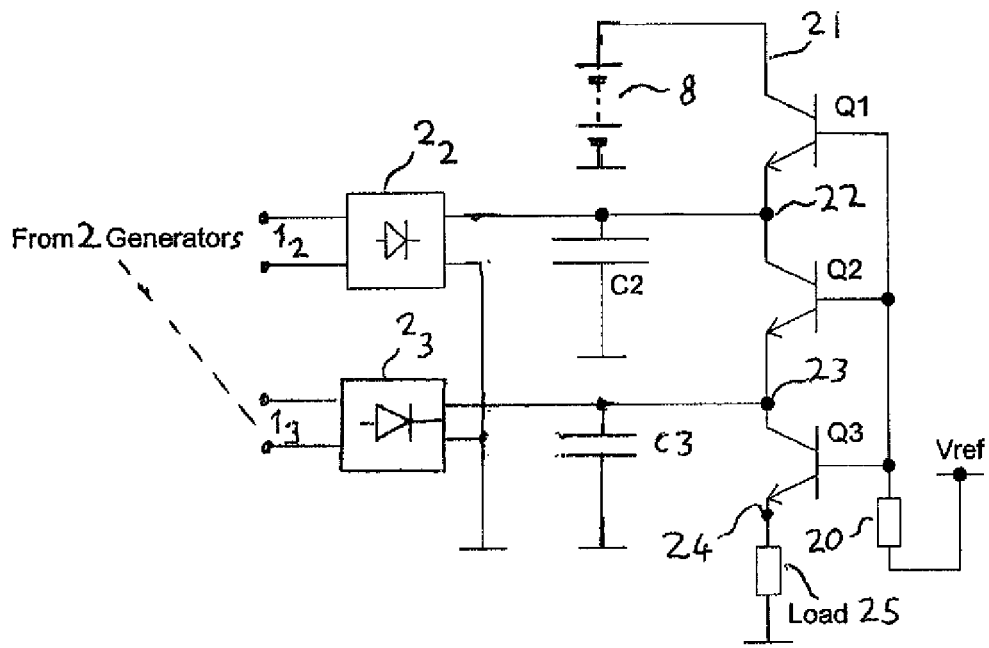
FIG. 4 is a circuit diagram of a control circuit and power supply constituting a second embodiment of the invention.

In applications where battery back-up is required, the regulator and power supply may be modified to include a battery which assists in providing continuous supply of power to the load irrespective of the availability of ambient energy. FIG. 4 illustrates a power supply of the type shown in FIG. 3 but modified to include a battery 8. The storage capacitors act as charge storage devices and, in the arrangement shown in FIG. 4, the first generator, the input $1_1$, the bridge rectifier $2_1$ and the capacitor C1 are omitted. Instead, the first circuit node 21 is connected to the battery 8 which acts as a charge storage device.

In use, the capacitor C3 shown in FIG. 4 initially supplies the load 25. As the voltage across the capacitor C3 falls, current is supplied first from the Capacitor C2 and then from the battery 8 so as to maintain the voltage across the load 25.

Although the transistors Q1, Q2 and 03 are shown as being of the same conductivity type, any or all of the transistors may, in alternative embodiments, be of the opposite conductivity type.

Figure 5:
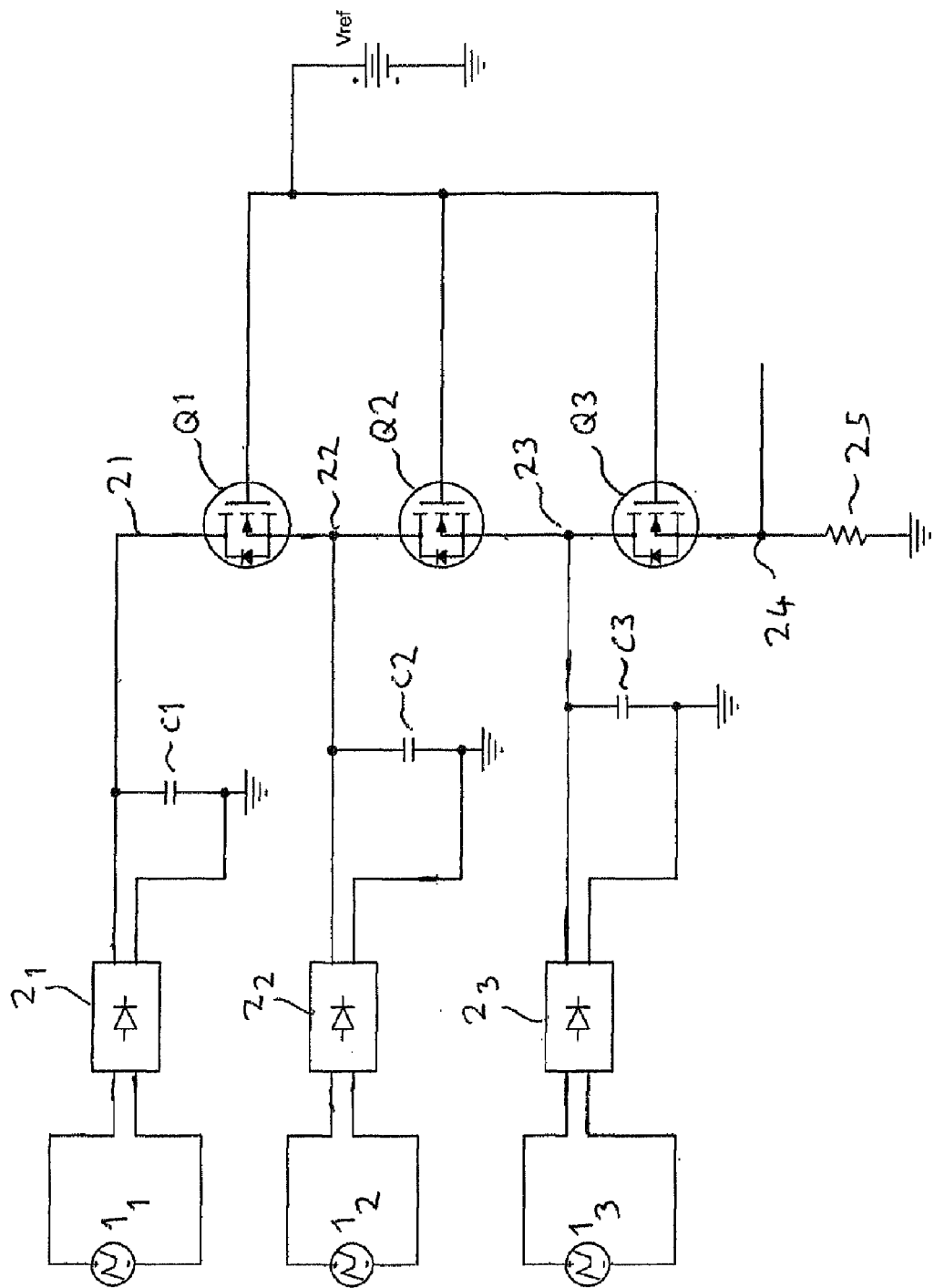
FIG. 5 is a circuit diagram of a control circuit and power supply constituting a third embodiment of the invention.

FIG. 5 illustrates a power supply of the type shown in FIG. 3. However, in this case, the transistors comprise MOSFETs Q1, Q2 and Q3 with their output terminals or drains connected to the circuit nodes 21, 22 and 23, respectively and their control or gate terminals connected together and directly to the voltage reference $V_{ref}$. The common or source terminals of the transistors Q1, Q2 and Q3 are connected to the second circuit node 22, the third circuit node 23 and the output 24, respectively.

One specific application for which the power supplies described hereinbefore are suitable is in medical electronic body implants, such as cardiac pacemakers. The generators may be used to scavenge energy from within the body so as to power, or augment the power, supplied to the electronics within the implant. For example, the generators may be arranged to scavenge energy from movement within the body. Such an arrangement may be used to prolong the life of an implant between replacements or servicing, for example to replace a battery.

Such arrangements make more efficient use of energy scavenged from the environment of the power generators. For example, even if one of the storage devices (storage capacitor or battery) is fully charged, the other storage devices may continue to be charged so that more energy may be scavenged and may be stored. By using an individual storage capacitor for each power generator, each such capacitor may have a reduced value as compared with the use of a single storage capacitor as in the known arrangements. Such smaller value capacitors reduce the stress on the power generators and allow a physically smaller package and faster charge-times to be achieved.

The power supply actively regulates the voltage supplied to the load in addition to controlling which of the storage devices contributes current to the load. Thus, it is not necessary to provide a separate regulator or regulator stage so that the complexity and cost may be reduced. The sequential use of capacitors may increase the time for which the load may be supplied and the generation of current peaks is eliminated or reduced, thus reducing the likelihood of generating electromagnetic interference. For small-scale applications, the voltage regulator may be made in the form of an application-specific integrated circuit (ASIC) so that a reduction or saving in size and/or cost may be achieved.

The power supply may be used for generators of different types simultaneously. Alternatively or additionally, generators of similar types but arranged in different ways may be used. For example, the generators may be arranged on different mechanical axes to improve the scavenging, or consistency of scavenging, of energy from the environment. In one example, three vibration source generators are mounted in mutually orthogonal directions, for example on a machine from which vibrational energy may be scavenged and converted into electrical energy.

Although the embodiments describe hereinbefore comprise three charge storage devices and three transistors, any number, greater than one, of such charge storage devices and transistors may be used according to the requirements of any application.

The invention claimed is

1. A control circuit for a power supply, comprising: an output; N circuit nodes where N is an integer greater than one; N charge storage devices; N amplifying devices, each of which has a main conduction path and a control terminal; a plurality of power inputs for connection to respective power generators; and a reference voltage input, said main conduction paths being connected in series and said control terminals being connected together to said reference voltage input, said main conduction path of an Nth one of said amplifying devices being connected between said output and an Nth one of said circuit nodes, which is connected to an Nth one of said charge storage devices, said main conduction path of each ith one of said amplifying devices, for each i such that $1 \leq i < N$, being connected between an (i+1)th one of said circuit nodes and an ith one of said circuit nodes, which is connected to an ith one of said charge storage devices, each of said power inputs being connected to a respective one of said circuit nodes.

2. A circuit as claimed in claim 1, in which at least some of said charge storage devices comprise capacitors.

3. A circuit as claimed in claim 2, in which all of said charge storage devices comprise capacitors.

4. A circuit as claimed in claim 1, in which at least one of said charge storage devices comprises a battery.

5. A circuit as claimed in claim 4, in which a first of said charge storage devices comprises said battery.

6. A circuit as claimed in claim 1, in which each of said amplifying devices has a common terminal and an output terminal and said output terminal of each jth one of said amplifying devices, for each j such that $i \leq j \leq N$. is connected to a jth one of said circuit nodes.

7. A circuit as claimed in claim 1, in which each of said amplifying devices comprises a semiconductor device.

8. A circuit as claimed in claim 6, in which each of said amplifying devices comprises a semiconductor device and said semiconductor devices are of a same conductivity type.

9. A circuit as claimed in claim 8, in which the semiconductor devices comprise transistors, said control terminals comprise one of base and gate terminals, said common terminals comprise one of emitter and source terminals, and said output terminals comprise one of collector and drain terminals.

10. A circuit as claimed in claim 1, comprising a rectifier having a rectifier input connected to a respective one of said inputs and a rectifier output connected to a respective one of said change storage devices and a respective one of said circuit nodes.

11. A power supply including a control circuit comprising: an output; N circuit nodes where N is an integer greater than one; N charge storage devices; N amplifying devices, each of which has a main conduction path and a control terminal; a plurality of power inputs for connection to respective power generators; and a reference voltage input, said main conduction paths being connected in series and said control terminals being connected together to said reference voltage input, said main conduction path of an Nth one of said amplifying devices being connected between said output and an Nth one of said circuit nodes, which is connected to an Nth one of said charge storage devices, said main conduction path of each ith one of said amplifying devices, for each i such that $1 \leq i < N$, being connected between an (i+1)th one of said circuit nodes and an ith one of said circuit nodes, which is connected to an ith one of said charge storage devices, each of said power inputs being connected to a respective one of said circuit nodes.

12. A supply as claimed in claim 11, comprising a plurality of power generators, each of which is connected to a respective one of said power inputs.

13. A supply as claimed in claim 12, in which each of said power generators comprises an energy scavenging generator.

14. A body implant including a power supply including a control circuit comprising: an output; N circuit nodes where N is an integer greater than one; N charge storage devices; N amplifying devices, each of which has a main conduction path and a control terminal; a plurality of power inputs for connection to respective power generators; and a reference voltage input, said main conduction paths being connected in series and said control terminals being connected together to said reference voltage input, said main conduction path of an Nth one of said amplifying devices being connected between said output and an Nth one of said circuit nodes, which is connected to an Nth one of said charge storage devices, said main conduction path of each ith one of said amplifying devices, for each i such that $1 \leq i < N$, being connected between an (i+1)th one of said circuit nodes and an ith one of said circuit nodes, which is connected to an ith one of said charge storage devices, each of said power inputs being connected to a respective one of said circuit nodes.

\* \* \* \* \*